(12) United States Patent
Singh et al.

(10) Patent No.: US 7,695,635 B2
(45) Date of Patent: *Apr. 13, 2010

(54) AZEOTROPE-LIKE COMPOSITIONS OF 1-CHLORO-3,3,3-TRIFLUOROPROPENE AND METHYL IODIDE

(75) Inventors: Rajiv R. Singh, Getzville, NY (US); Hang T. Pham, Amherst, NY (US); Andrew J. Poss, Kenmore, NY (US)

(73) Assignee: Honeywell International Inc, Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/258,537

(22) Filed: Oct. 27, 2008

(65) Prior Publication Data

US 2009/0041677 A1   Feb. 12, 2009

Related U.S. Application Data

(63) Continuation-in-part of application No. 11/707,498, filed on Feb. 16, 2007.

(51) Int. Cl.
*C09K 5/04* (2006.01)
*C11D 7/30* (2006.01)
*A01N 25/02* (2006.01)
*A01N 29/00* (2006.01)

(52) U.S. Cl. .............. 252/67; 252/68; 252/69; 510/177; 510/408; 510/412; 510/415; 424/405; 514/743; 514/744; 514/746

(58) Field of Classification Search ........... 252/67, 252/68, 69; 510/177, 408, 412, 415; 424/405; 514/743, 744, 746

See application file for complete search history.

(56) References Cited

U.S. PATENT DOCUMENTS

| 5,158,617 A | * | 10/1992 | Li ................ 134/40 |
| 5,316,690 A | * | 5/1994 | Li ............... 510/412 |
| 5,518,692 A | | 5/1996 | Grech et al. ........ 422/37 |
| 5,705,716 A | * | 1/1998 | Li ............... 570/134 |
| 5,753,183 A | | 5/1998 | Ohr et al. ........... 422/37 |
| 6,465,527 B1 | | 10/2002 | Rodriguez-Kabana et al. ........... 514/743 |
| 6,984,768 B2 | * | 1/2006 | Ginosar et al. ....... 588/316 |
| 7,544,306 B2 | * | 6/2009 | Poss et al. .......... 252/67 |
| 2005/0085674 A1 | * | 4/2005 | Nakada et al. ........ 570/178 |
| 2005/0228027 A1 | * | 10/2005 | Zhu et al. ........... 514/342 |
| 2008/0110833 A1 | | 5/2008 | Samuels et al. |
| 2008/0111099 A1 | * | 5/2008 | Singh et al. ......... 252/67 |
| 2008/0199408 A1 | | 8/2008 | Poss et al. .......... 424/40 |

FOREIGN PATENT DOCUMENTS

| WO | 99/42144 | 8/1999 |
| WO | WO2006/028293 | 3/2006 |

OTHER PUBLICATIONS

Reg. No. 74-88-4, Nov. 16, 1984.*
Reg. No. 406-58-6, Nov. 16, 1984.*
Reg. No. 460-73-1, Nov. 16, 1984.*
Reg. No. 2730-43-0, Nov. 16, 1984.*
Reg. No. 29118-25-0, Nov. 16, 1984.*
"Dose Response of Weeds To Methyl Iodide and Methyl Bromide." W.M. Zhang, et al., Weed Research, 1997, vol. 37, 181-189.
"Effect of Soil Physical Factors On Methyl Iodide and Methyl Bromide." Wenming Zhang, et al., Pestic. Sci. 1998, 53, 71-79.
"Methyl Iodide, an Ozone-Safe Alternative To Methyl Bromide As a Soil Fumigant." H.D. Ohr, et al., Plant Disease 80: 731-735. Jul. 1996.
"Methyl Iodide: An Alternative To Methyl Bromide For Insectary Fumigation." M. Waggoner, et al., J. Appl. Ent. 124,, 113-117 (2000).

* cited by examiner

*Primary Examiner*—Douglas Mc Ginty
(74) *Attorney, Agent, or Firm*—Bruce Bradford

(57) ABSTRACT

An azeotropic or azeotrope-like composition comprising a mixture of methyl iodide, 1-chloro-3,3,3,-trifluoropropene, and optionally one or more of fluorocarbons and/or hydrofluorocarbons. The compositions are present as a gas, at temperatures of about 30° C. or below. The inventive compositions serve as a non-ozone-depleting gaseous fumigant which is useful in a variety of applications, in place of methyl bromide. These compositions serve as a drop-in replacement for gaseous methyl bromide, providing the benefits of a methyl iodide fumigant while also utilizing existing methyl bromide equipment.

19 Claims, No Drawings

AZEOTROPE-LIKE COMPOSITIONS OF 1-CHLORO-3,3,3-TRIFLUOROPROPENE AND METHYL IODIDE

CROSS REFERENCE TO RELATED APPLICATION

This application is a Continuation-In-Part of U.S. patent application Ser. No. 11/707,498 filed Feb. 16, 2007, which is incorporated herein by reference.

BACKGROUND OF THE INVENTION

1. Field of the Invention

The present invention relates to fumigants, and particularly to fumigant compositions having similar properties to methyl bromide, without its ozone-depleting properties. Specifically, the invention relates to azeotropic or azeotrope-like composition of methyl iodide, 1-chloro-3,3,3,-trifluoropropene (HFO-1233zd(E)) and optionally one or more fluorocarbons or hydrofluorocarbons.

2. Description of the Related Art

Methyl Bromide is a gaseous fumigant that has been used commercially since the early 1900's. It is known for being extremely effective as a herbicide, nematocide, insecticide and fungicide. Methyl bromide has been widely used for soil fumigation, not only for controlling a variety of pests on numerous crops, but also as a commodity quarantine treatment for imports and exports, and as a structural fumigant applied to a building surface or the like.

However, it is a Restricted Use Pesticide (RUP) because of its high acute toxicity to applicators. Methyl bromide has also been designated as an ozone-depleter, and thus its production and use have been severely restricted pursuant to the Montreal Protocol.

Efforts have been made to develop an alternative or replacement for methyl bromide as a fumigant. There currently exist only a few conventional methyl bromide alternatives, such as chloropicrin, 1,3-dichloropropene, metham sodium, and methyl iodide. Two or more of these materials are commonly applied as a mixture, to produce a product similar to methyl bromide. However, none of these potential alternatives are an adequate "drop-in replacement" for methyl bromide, based on their physical handling requirements, performance, or economics. The term "drop-in replacement" is used when the methodology, equipment, production system, and the like, of an original material do not have to be changed significantly when using a replacement material, and that a comparable amount of the replacement material can be used for the same targets as the original material.

A great deal of research has been conducted in evaluating methyl iodide as a drop-in replacement for methyl bromide. Methyl iodide has been found to be equal to or better than methyl bromide in combating weeds, nematodes, and soil pathogens. Further, methyl iodide is not associated with ozone depletion, and does not result in plant toxicity when used in effective concentrations. However, methyl iodide is a low boiling liquid with a boiling point of 42.5° C. (108° F.), while methyl bromide is a gas at ambient temperature and pressure. Methyl iodide has a lower vapor pressure and higher density than methyl bromide. Thus, the use of methyl iodide in existing methyl bromide equipment suffers several shortcomings such as clogged tubing, material remnants in system pipes, and long line purging processes for cleaning. Furthermore, the use of methyl iodide results in problems such as missed bed applications, since the methyl bromide equipment is designed for gaseous fumigant applications. Such missed bed applications may lead to significant crop loss in soil fumigation. Thus, while methyl iodide may serve well as a fumigant, it is not a suitable drop-in replacement for methyl bromide.

It would be desirable to provide a fumigant alternative to methyl bromide which can also serve as a drop-in replacement, thereby allowing for the use existing methyl bromide equipment and systems. The present invention provides a solution to this problem.

It has now been unexpectedly found that by combining methyl iodide with 1-chloro-3,3,3,-trifluoropropene (HFO-1233zd(E)) and optionally one or more fluorocarbons or hydrofluorocarbons., the resulting azeotropic or azeotrope-like composition exists as a gas at temperatures below about 30° C. The resulting gaseous composition serves as a drop-in replacement for methyl bromide, providing benefits if a methyl iodide fumigant while also utilizing existing methyl bromide equipment.

SUMMARY OF THE INVENTION

The invention provides an azeotropic or azeotrope-like composition comprising a mixture of methyl iodide, 1-chloro-3,3,3,-trifluoropropene, and optionally one or more of fluorocarbons and/or hydrofluorocarbons, which composition is a gas at temperatures of about 30° C. or below.

The invention further provides a fumigation process which comprises:

a) providing a fumigant comprising an azeotropic or azeotrope-like composition comprising a mixture of methyl iodide, 1-chloro-3,3,3,-trifluoropropene, and optionally one or more of fluorocarbons and/or hydrofluorocarbons, which composition is a gas at temperatures of about 30° C. or below; and b) applying the fumigant to a material to be fumigated.

DETAILED DESCRIPTION OF THE INVENTION

The invention relates to an azeotropic or azeotrope-like composition comprising a mixture of methyl iodide, 1-chloro-3,3,3,-trifluoropropene, and optionally one or more of fluorocarbons and/or hydrofluorocarbons, which composition is a gas at temperatures of about 30° C. or below.

As used herein, the term "azeotrope-like" is intended in its broad sense to include both compositions that are strictly azeotropic and compositions that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at the stated pressure and temperature. In practice, this means that the components of an azeotropic mixture are constant boiling and cannot be separated during distillation.

Azeotrope-like compositions are constant boiling or essentially constant boiling. In other words, for azeotrope-like compositions, the composition of the vapor formed during boiling or evaporation (under substantially isobaric conditions) is identical, or substantially identical, to the original liquid composition. Thus, with boiling or evaporation, the liquid composition changes, if at all, only to a minimal or negligible extent. This is to be contrasted with non-azeotrope-like compositions in which, during boiling or evaporation, the liquid composition changes to a substantial degree. All azeotrope-like compositions of the invention within the indicated ranges as well as certain compositions outside these ranges are azeotrope-like.

It is well known that at differing pressures, the composition of a given azeotrope will vary at least slightly, as does the boiling point of the composition. Thus, an azeotrope of A and B represents a unique type of relationship, but with a variable composition depending on temperature and/or pressure. It follows that, for azeotrope-like compositions, there is a range of compositions containing these components in varying proportions that are azeotrope-like. All such compositions are intended to be covered by the term azeotrope-like as used herein.

As stated above, the present invention provides an azeotropic or azeotrope-like composition comprising a mixture of methyl iodide, 1-chloro-3,3,3,-trifluoropropene, and optionally one or more of fluorocarbons and/or hydrofluorocarbons. Methyl iodide, also known as iodomethane, which is commonly abbreviated as "MeI" and has the formula $CH_3I$. Methyl iodide has a boiling point of about 42.5° C. and a density of about 2.3 g/cc. Methyl iodide has been conventionally known as a useful fumigant, and serves this purpose in the inventive composition. An added benefit of methyl iodide is that it is not associated with ozone depletion.

Fluorocarbons are defined herein as any carbon molecule having at least one attached fluorine group. Hydrofluorocarbons are particularly useful in the present invention. The present claims require that the inventive compositions optionally comprise at least one fluorocarbon or hydrofluorocarbon. The HFO-1233zd(E) and the optional at least one fluorocarbon or hydrofluorocarbon increases the overall volume of the inventive compositions, facilitating application of the composition and increasing the time that a given volume of methyl iodide is exposed to a material to be contacted. The HFO-1233zd(E) and the optional at least one fluorocarbon or hydrofluorocarbon further enables a more uniform and easily controlled application of the inventive composition. In addition, the HFO-1233zd(E) and the optional at least one fluorocarbon or hydrofluorocarbon serves as a non-toxic portion of the composition, reducing worker exposure to toxic materials.

Several different fluorocarbons and hydrofluorocarbons may be suitable for use in the compositions formed according to this invention. Examples of suitable fluorocarbons for use in the present invention nonexclusively include HFO-1233zd (Z), 1-chloro-3,3,3 trifluoropropene (HCFC-1233xd); 2,2-dichloro-1,1,1-trifluoroethane (HCFC-123); 1,1,2,2-tetrafluoroethyl methyl ether (HFE-245); and cis-1,3,3,3-tetrafluoropropene (HFC-1234ze). Examples of suitable hydrofluorocarbons for use in the present invention nonexclusively include 1,1,1,3,3-pentafluoropropane (HFC-245fa); 1,1,1,3,3-pentafluorobutane (HFC-365); 1,2-difluoroethane (HFC-152); 1,2,2,3,3-pentafluoropropane (245ca); and 1,2,2-trifluoroethane (HFC-143). A preferred hydrocarbon is 1,1,1,3,3-pentafluoropropane (HFC-245fa), which is a nonflammable and non-toxic compound with an ozone depletion potential of zero. It has been unexpectedly found that methyl iodide and HFO-1233zd(Z), form an azeotropic mixture which closely resembles several physical properties of methyl bromide, such as specific gravity and density. It has also been found that methyl iodide; HFO-1233zd(Z), and at least one of 1,1,1,3,3-pentafluoropropane (HFC-245fa); 1,1,3,3-pentafluorobutane (HFC-365) and cis-1,3,3,3-tetrafluoropropene (HFC-1234ze) form an azeotropic mixture which resembles the properties of methyl bromide. In a preferred embodiment, the optional fluorocarbon or hydrofluorocarbon has a boiling point of from about 0° C. to about 50° C.

In preferred embodiments, the HFO-1233zd(E) and the optional fluorocarbon or hydrofluorocarbon has an average Ozone Depletion Potential (ODP) of about 0.05 or less, preferably about zero. The ozone depletion potential (ODP) of a chemical compound is the relative amount of degradation to the ozone layer it can cause, with trichlorofluoromethane (R-11) being fixed at an ODP of 1.0. Chlorodifluoromethane (R-22), for example, has an ODP of 0.05.

In further preferred embodiments, the HFO-1233zd(E) and the optional fluorocarbon or hydrofluorocarbon has a 100-year Global Warming Potential (GWP) of about 1,000 or less, preferably 20 or less. Global warming potential (GWP) is a measure of how much a given mass of greenhouse gas is estimated to contribute to global warming. It is a relative scale which compares the gas in question to that of the same mass of carbon dioxide, whose GWP is 1 by definition. A GWP is calculated over a specific time interval and the value of this must be stated whenever a GWP is quoted. The most common time interval used today is 100 years.

The compositions of the present invention comprise effective amounts of the methyl iodide; HFO-1233zd(E) and the optional fluorocarbon or hydrofluorocarbon. The term "effective amounts" as used herein refers to the amount of each component which, upon combination with the other component or components, results in the formation of the presently claimed azeotropic or azeotrope-like compositions. The methyl iodide is preferably present in the inventive composition an amount from about 0.3 to about 50 weight percent of the composition, more preferably from about 1 to about 30 weight percent, and most preferably from about 2 to about 10 weight percent. When the inventive composition does not contain any optional fluorocarbon or hydrofluorocarbon, the HFO-1233zd(E) is preferably present in the composition in an amount from about 50 to about 99.7 weight percent of the composition, more preferably from about 70 to about 99 weight percent of the composition, and most preferably from about 90 to about 98 weight percent of the composition.

When the inventive composition does contain optional fluorocarbon or hydrofluorocarbon, the HFO-1233zd(E) is preferably present in the composition in an amount from about 10 to about 98.7 weight percent of the composition, more preferably from about 35 to about 94 weight percent of the composition, and most preferably from about 60 to about 88 weight percent of the composition. In this case, the fluorocarbon or hydrofluorocarbon, is preferably present in the composition in an amount from about 1 to about 40 weight percent of the composition, more preferably from about 5 to about 35 weight percent of the composition, and most preferably from about 10 to about 30 weight percent of the composition.

In one embodiment, the inventive compositions may be present in the form of binary azeotropic or azeotrope-like compositions, which consist essentially of methyl iodide and HFO-1233zd(E). In another embodiment, the inventive compositions may be present in the form of azeotropic or azeotrope-like compositions, which consist essentially of methyl iodide, HFO-1233zd(E) and at least one fluorocarbon or hydrofluorocarbon.

The fumigant compositions of the invention may optionally include additional components or additives. Suitable additives for the present compositions nonexclusively include chloropicrin, acrolein, 1,3-dichloropropene, dimethyl disulfide, furfural, and propylene oxide. One preferred additive includes chloropicrin. The optional additive included in the fumigant composition may be present in an amount of from about 0 wt. % to about 40 wt. %, preferably from about 0.5 wt. % to about 5 wt. % and more preferably from about 1 wt % to about 3 wt. %. For example, in one preferred embodiment, a fumigant composition of the invention comprises 33 wt. % methyl iodide, 33 wt. % HFO-1233zd(E), and 33 wt. % chloropicrin.

The methyl iodide, HFO-1233zd(E), the optional at least one fluorocarbon or hydrofluorocarbon, and any optional additives, may be combined using any conventional means which results in a substantially homogeneous mixture of all components. When combined, the inventive mixture preferably forms an azeotropic or azeotrope-like composition which is present in the form of a gas at temperatures of about 30° C. or below.

The inventive compositions are present preferably in the form of a gas at temperatures of about 30° C. or below, and in certain embodiments preferably at about 25° C. or below, such that the compositions may be applied in a gaseous state at room temperature, and utilize methyl bromide equipment systems which were designed for gaseous applications. In a preferred embodiment, the compositions of the present invention have a boiling point which ranges from about 17° C. to about 20° C., more preferably from about 17.5° C. to about 18.5° C., and most preferably from about 17.7° C. to about 18° C. at 14.4 psia pressure.

The inventive compositions preferably exhibit a particular density which allows for the compositions to be used in methyl bromide equipment systems without causing blockages and the like. In a preferred embodiment, the compositions of the present invention have a density of from about 1.6 g/cc to about 2.4 g/cc, more preferably from about 1.7 g/cc to about 2.2 g/cc, and most preferably from about 1.6 g/cc to about 2.0 g/cc at 20° C.

The inventive compositions may be used in a variety of applications. These compositions are particularly suited for use as a fumigant or as a component of a fumigant. Examples of fumigation applications for the inventive compositions nonexclusively include combating insects, termites, rodents, weeds, nematodes, and soil-borne diseases. The compositions may further be used to fumigate agricultural commodities, grain elevators, mills, ships, clothes, furniture, greenhouses, and the control of pests in buildings (structural fumigation), and the like.

The inventive compositions are preferably pumped through existing fumigation pipes and systems designed for methyl bromide use. The inventive gaseous compositions eliminate the problems of clogged tubing, pooled deposits of chemicals that are typically associated with liquid methyl iodide, and can be easily purged from the system. In fact, methyl iodide's particular difficulty of missed bed application is no longer a problem because the inventive azeotropic or azeotrope-like compositions, like methyl bromide, are present as a gas at ambient temperature and move easily through application tubing of an existing methyl bromide system. Furthermore, the inventive azeotropic or azeotrope-like compositions have a very similar environmental efficacy and spectrum of activity as methyl bromide, while also exhibiting a low potential for ozone degradation. Thus, the inventive compositions effectively serve as a drop-in replacement for methyl bromide.

The present invention further relates to a fumigation process. According to this process, a fumigant is provided which comprises an azeotropic or azeotrope-like composition which comprises a mixture of methyl iodide, HFO-1233zd(E), and at least one fluorocarbon or hydrofluorocarbon, which composition is a gas at temperatures of about 30° C. or below. The fumigant preferably comprises or consists essentially of the azeotropic or azeotrope-like compositions discussed at length above. The fumigant is then applied to a material to be fumigated, and is preferably applied in the form of a gas. In a preferred embodiment, the application of the fumigant is conducted at an ambient temperature of from about 0° C. to about 50° C. The fumigant may be applied to a variety of different materials to be fumigated, in a variety of fumigation applications as described above. In one preferred embodiment, the fumigant is applied to soil. In a further preferred embodiment the fumigant is applied to wood. In still another preferred embodiment the fumigant is applied to a building surface.

The following non-limiting examples serve to illustrate the invention. It will be appreciated that variations in proportions and alternatives in elements of the components of the invention will be apparent to those skilled in the art and are within the scope of the present invention.

EXAMPLE 1

An ebulliometer composed of a vacuum jacketed tube with a condenser on top which was further equipped with a Quartz Thermometer was used. About 20 g HFO-1233zd(E) is charged into the ebulliometer and then methyl iodide was added in small, measured increments, at an atmospheric pressure of 14.4 psia. A temperature depression was observed when methyl iodide was added to HFO-1233zd (E), indicating a binary minimum boiling azeotrope had been formed. From greater than 0 to about 30 weight percent methyl iodide, the boiling point of the composition changes less than about 0.5 ° C., with a minimum in the boiling point curve being around 2 to 6 wt % $CH_3I$. Thus the compositions exhibited azeotrope and/or azeotrope-like properties over these ranges. Results are in Table 1.

TABLE 1

HFO-1233zd(E)/methyl Iodide compositions at 14.40 psia

| Wt. % $CH_3I$ | Wt. % HFO-1233zd (E) | | T (C) |
|---|---|---|---|
| 0.00 | 100.00 | | 17.75 |
| 0.56 | 99.90 | | 17.75 |
| 1.67 | 98.78 | | 17.74 |
| 3.81 | 96.63 | <---- AZ Comp. | 17.74 |
| 5.86 | 94.57 | | 17.76 |
| 9.72 | 90.70 | | 17.81 |
| 14.11 | 86.29 | | 17.90 |
| 18.09 | 82.29 | | 17.99 |
| 23.75 | 76.60 | | 18.12 |
| 28.68 | 71.65 | | 18.20 |

EXAMPLE 2

Methyl iodide and HFO-1233zd(E) are combined to form an azeotrope or azeotrope-like composition according to the present invention. The composition is applied as a fumigant to a field prior to planting the soil, by injection through shank-mounted tubes that are pulled through the soil, followed by covering the soil with a plastic film. The fumigant is applied at a broadcast rate sufficient to rid the soil of any diseases and pests found therein. After the fumigant is applied, the soil is to remain undisturbed for a sufficient time to allow the fumigant to rid the soil of all deleterious organisms. Applications to the soil include attention to soil conditions such as high moisture content, soil temperatures below 13° C./55° F. at a 20 cm/8-inch depth, and/or cloddy soils with high plant /weed trash content. The treated field may be planted after the elapsed planting interval time.

EXAMPLE 3

Methyl iodide, HFO-1233zd(E), and chloropicrin are combined to form an azeotrope or azeotrope-like composition according to the present invention. The composition is applied as a fumigant to a field prior to planting the soil, by injection through shank-mounted tubes that are pulled through the soil, followed by covering the soil with a plastic film. The fumigant is applied at a broadcast rate sufficient to rid the soil of any diseases and pests found therein. After the fumigant is applied, the soil is to remain undisturbed for a sufficient time to allow the fumigant to rid the soil of all deleterious organisms. Applications to the soil include attention to soil conditions such as high moisture content, soil temperatures below 13° C./55° F. at a 20 cm/8-inch depth, and/or cloddy soils with high plant /weed trash content. The treated field may be planted after the elapsed planting interval time.

EXAMPLE 4

Methyl iodide and HFO-1233zd(E) are combined to form an azeotrope or azeotrope-like composition according to the present invention. The composition is applied as a fumigant to a field, prior to planting the soil, in water through the drip irrigation system under a plastic tarp. The fumigant is applied at a broadcast rate sufficient to treat to rid the soil of any diseases and pests found therein. After the fumigant is applied, the soil should remain undisturbed for a sufficient time to allow the fumigant to rid the soil of all deleterious organisms. Applications to the soil include attention to soil conditions such as high moisture content, soil temperatures below 13° C./55° F. at a 20 cm/8-inch depth, and/or cloddy soils with high plant /weed trash content. The treated field may be planted after the elapsed planting interval time.

EXAMPLE 5

Methyl iodide, HFO-1233zd(E), and chloropicrin are combined to form an azeotrope or azeotrope-like composition according to the present invention. The composition is applied as a fumigant to a field, prior to planting the soil, in water through the drip irrigation system under a plastic tarp. The fumigant is applied at a broadcast rate sufficient to treat to rid the soil of any diseases and pests found therein. After the fumigant is applied, the soil should remain undisturbed for a sufficient time to allow the fumigant to rid the soil of all deleterious organisms. Applications to the soil include attention to soil conditions such as high moisture content, soil temperatures below 13° C./55° F. at a 20 cm/8-inch depth, and/or cloddy soils with high plant /weed trash content. The treated field may be planted after the elapsed planting interval time.

EXAMPLE 6

This example relates to a structural fumigation process. Prior to structural fumigation, all open flames and glowing heat filaments are turned off or disconnected. Methyl iodide and HFO-1233zd(E) are combined to form an azeotrope or azeotrope-like composition according to the present invention. The composition is applied as a fumigant to tarped or sealed structures for an exposure period necessary to rid the structure of all deleterious organisms, followed by an aeration period long enough to flush the unused fumigant and any warning gas from the structure. Because the methyl iodide/HFO-1233zd(E) mixture is odorless and does not irritate the eyes or skin, trace amounts of a warning agent (e.g. chloropicrin) are introduced into the structure prior to fumigation to act as a warning agent. The required dosage of the fumigant is influenced by the temperature at the site of the pest, the length of the exposure period, containment or the rate the fumigant is lost from the structure, and the susceptibility of the pest to be controlled.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. An azeotropic or azeotrope-like composition consisting essentially of a mixture of from about 0.3 to about 30 weight percent methyl iodide, from about 99.7 to about 70 weight percent 1-chloro-3,3,3,-trifluoropropene, and optionally one or more of fluorocarbons and/or hydrofluorocarbons, which composition is a gas at temperatures of about 30° C. or below.

2. The composition of claim 1 wherein the optional one or more fluorocarbons and/or hydrofluorocarbons are present and have a boiling point of from about 0° C. to about 50° C.

3. The composition of claim 2 wherein the one or more fluorocarbons or hydrofluorocarbons have an average Ozone Depletion Potential of about 0.05 or less.

4. The composition of claim 2 wherein the one or more fluorocarbons or hydrofluorocarbons have a 100-year Global Warming Potential of about 1,000 or less.

5. The composition of claim 2 wherein the one or more fluorocarbons or hydrofluorocarbons consists essentially of at least one of 1,1,1,3,3-pentafluoropropane;
  1,1,1,3,3-pentafluorobutane or cis-1,3 ,3,3-tetrafluoropropene.

6. An azeotropic or azeotronic-like composition consisting essentially of from about 0.3 to about 50 weight percent methyl iodide, from about 10 to about 98.7 weight percent of 1-chloro-3,3,3,-trifluoropropene, and from about 1 to about 40 weight percent of the at least one fluorocarbon or hydrofluorocarbon.

7. The composition of claim 1 which has a boiling point of from about 17° C. to about 20° C.

8. The composition of claim 1 which has a density of from about 1.6 g/cc to about 2.4 g/cc.

9. A fumigant consisting essentially of the composition of claim 1.

10. A fumigant consisting essentially of the composition of claim 2.

11. A fumigant consisting essentially of the composition of claim 6, which composition consists essentially of from about 0.3 to about 50 weight percent methyl iodide; about 10 to about 98.7 weight percent of 1-chloro-3,3,3,-trifluoropropene and from about 1 to about 40 weight percent of the at least one fluorocarbon or hydrofluorocarbons; a density of from about 1.6 g/cc to about 2.4 g/cc; and wherein the at least one fluorocarbon or hydrofluorocarbon of the composition has an average Ozone Depletion Potential of about 0.05 or less, and a 100-year Global Warming Potential of about 1,000 or less.

12. The fumigant of claim 11 wherein the one or more fluorocarbons or hydrofluorocarbons consists essentially of at least one of 1,1,1,3,3-pentafluoropropane;

1,1,1,3,3-pentafluorobutane and cis-1,3,3,3-tetrafluoropropene.

13. The fumigant of claim 11 further consisting essentially of at least one of chloropicrin, acrolein, 1,3-dichloropropene, dimethyl disulfide, furfural, and propylene oxide.

14. A fumigation process which comprises:
   a) providing a fumigant consisting essentially of an azeotropic or azeotrope-like composition consisting essentially of a mixture of from about 0.3 to about 30 weight percent methyl iodide, from about 99.7 to about 70 weight percent 1-chloro-3,3,3,-trifluoropropene, and optionally one or more of fluorocarbons and/or hydrofluorocarbons, which composition is a gas at temperatures of about 30° C. or below; and
   b) applying the fumigant to a material to be fumigated.

15. The process of claim 14 wherein the fumigant consists essentially of at least one of chloropicrin, acrolein, 1,3-dichloropropene, dimethyl disulfide, furfural, and propylene oxide.

16. The process of claim 14 wherein the fumigant is applied in step (b) as a gas.

17. The process of claim 14 wherein step (b) is conducted at an ambient temperature of from about 0° C. to about 50° C.

18. The process of claim 14 wherein the one or more fluorocarbons or hydrofluorocarbons comprises at least one of 1,1,1,3,3-pentafluoropropane;

1,1,1,3,3-pentafluorobutane or cis- 1,3,3,3-tetrafluoropropene.

19. The process of claim 14 wherein the fumigant is applied to soil, wood or a building surface in step (b).

* * * * *